(12) United States Patent
Bulut et al.

(10) Patent No.: US 12,290,379 B2
(45) Date of Patent: May 6, 2025

(54) QUANTIFICATION AND ESTIMATION BASED ON DIGITAL TWIN OUTPUT

(71) Applicant: KONINKLIJKE PHILIPS N.V., Eindhoven (NL)

(72) Inventors: Murtaza Bulut, Eindhoven (NL); Cornelis Petrus Hendriks, Eindhoven (NL); Lieke Gertruda Elisabeth Cox, Eindhoven (NL); Valentina Lavezzo, Heeze (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1210 days.

(21) Appl. No.: 17/097,058

(22) Filed: Nov. 13, 2020

(65) Prior Publication Data

US 2021/0241116 A1    Aug. 5, 2021

Related U.S. Application Data

(60) Provisional application No. 62/970,402, filed on Feb. 5, 2020.

(51) Int. Cl.
*G06N 3/08* (2023.01)
*A61B 5/00* (2006.01)
(Continued)

(52) U.S. Cl.
CPC .......... *A61B 5/4824* (2013.01); *G06F 3/015* (2013.01); *G06F 18/2113* (2023.01); *G06F 30/27* (2020.01); *G06N 3/084* (2013.01)

(58) Field of Classification Search
CPC ................ G06N 3/02; G06N 3/0464
See application file for complete search history.

(56) References Cited

U.S. PATENT DOCUMENTS 6,911,006 B2   6/2005 Miyata et al.
11,042,980 B1 * 6/2021 Douglas ............... G06T 7/0016
(Continued)

FOREIGN PATENT DOCUMENTS

WO   WO-2016124482 A1 * 8/2016 ........... A61B 5/1118
WO   WO-2016151494 A1 * 9/2016

OTHER PUBLICATIONS

Buldakova et al.—"Hierarchy of Human Operator Models for Digital Twin", IEEE Xplore, Sep. 14, 2019, pp. 1-5. (Year: 2019).*
(Continued)

*Primary Examiner* — Paulinho E Smith (57) ABSTRACT

Embodiments are described herein for training machine learning models using digital twin outputs, including for purposes of pain quantification and estimation. In various embodiments, simulation parameter(s) may be applied to a digital twin created for a subject. The digital twin may simulate an anatomical structure of the subject, and the simulation parameter(s) may cause the digital twin to generate digital twin output that simulates behavior of the anatomical structure in response to the one or more simulation parameters. Data indicative of the digital twin output may be applied as input across a pain estimation machine learning model to generate pain estimation output. Based on the pain estimation output, a quantification of pain, e.g., an estimated pain score, may be rendered using an output device and/or used to select a treatment plan.

9 Claims, 8 Drawing Sheets

(51) Int. Cl.
  *G06F 3/01* (2006.01)
  *G06F 18/2113* (2023.01)
  *G06F 30/27* (2020.01)
  *G06N 3/084* (2023.01)

(56) References Cited

U.S. PATENT DOCUMENTS

| | | | | |
|---|---|---|---|---|
| 11,687,800 | B2 * | 6/2023 | Bonutti | G08B 31/00 |
| | | | | 706/11 |
| 11,704,582 | B1 * | 7/2023 | Jain | G16H 50/20 |
| | | | | 705/2 |
| 2011/0270770 | A1 * | 11/2011 | Cunningham | G06Q 30/016 |
| | | | | 706/12 |
| 2012/0030156 | A1 * | 2/2012 | Udink | G16H 50/30 |
| | | | | 706/45 |
| 2013/0310660 | A1 | 11/2013 | Kliger et al. | |
| 2017/0135631 | A1 * | 5/2017 | Zuckerman-Stark | |
| | | | | A61B 5/4824 |
| 2017/0316164 | A1 * | 11/2017 | Casale | A61B 5/7264 |
| 2018/0330800 | A1 * | 11/2018 | Bogue | G16H 10/20 |
| 2019/0065970 | A1 * | 2/2019 | Bonutti | G08B 31/00 |
| 2019/0343457 | A1 * | 11/2019 | Rahmani | G06N 3/08 |
| 2021/0030354 | A1 * | 2/2021 | Alzamzmi | A61B 5/4824 |
| 2021/0124465 | A1 * | 4/2021 | Sahu | G06F 3/0482 |
| 2022/0138583 | A1 * | 5/2022 | Hernandez Rivera | |
| | | | | G06N 3/045 |
| | | | | 706/20 |
| 2023/0273974 | A1 * | 8/2023 | Robinson | G06N 3/08 |
| | | | | 706/15 |
| 2024/0138919 | A1 * | 5/2024 | Casey | G16H 50/50 |
| 2024/0225848 | A1 * | 7/2024 | Bogue | A61B 17/92 |

OTHER PUBLICATIONS

Lopez-Martinez et al.—"Multi-task Neural Networks for Personalized Pain Recognition from Physiological Signals", 2017 Seventh International Conference on Affective Computing and Intelligent Interaction Workshops and Demos (ACIIW), Sep. 4, 2017, pp. 1-4. (Year: 2017).*

Thiam et al., "Exploring Deep Physiological Models for Nociceptive Pain Recognition", Oct. 17, 2019, Sensors, pp. 1-21 (Year: 2019).*

Lopez-Martinez et al., "Physiological and behavioral profiling for nociceptive pain estimation using personalized multitask learning", Nov. 10, 2017, ArXiv, pp. 1-6 (Year: 2017).*

Lopez-Martinez et al., "Continuous Pain Intensity Estimation from Autonomic Signals with Recurrent Neural Networks", Jul. 2018, pp. 1-4 (Year: 2018).*

* cited by examiner

QUANTIFICATION AND ESTIMATION BASED ON DIGITAL TWIN OUTPUT

TECHNICAL FIELD

Various embodiments described herein are directed generally to health care, digital twins, and/or machine learning. More particularly, but not exclusively, various methods and apparatus disclosed herein relate to quantification and estimation based on digital twin output, including determination of estimated pain scores.

BACKGROUND

Various metrics may be difficult to estimate, e.g., because they are subjective in nature and/or are dependent on a large number of factors that interplay with each other in complex ways. For example, pain quantification is a difficult problem because pain is generally a subjective observation, and the living things that experience pain are highly complex systems. Attempts have been made to analyze various physiological signals to predict a subject's experience of pain. For example, the firing of spinal cord neurons has been used to attempt to quantify a measure of pain experienced by a subject. However, these techniques are limited in scope and do not facilitate estimation of pain that a subject will experience if the subject is treated with a given therapy.

SUMMARY

The present disclosure is directed to methods and apparatus for quantification and estimation based on digital twin output. For example, in various embodiments, outputs of a biophysical model (e.g., a digital twin) of an anatomical structure or system may be analyzed to train machine learning model(s) to estimate a quantified amount of pain a subject is likely to experience, given application of particular stimuli to the biophysical model.

The use of digital models such as digital twins provides for a number of technical advantages. Digital twins allow for estimation of hard to measure parameters (e.g., pain) because they enable many different digital twin outputs to be generated (as a result of simulations) without disturbing the physical object (e.g., a patient). Consequently, it is possible to test myriad output options to find the particular outputs that are best-suited in a particular context to predict hard-to-measure parameters such as subjective pain. Put another way, digital twins allow for the possibility of conducting many different "digital experiments" on a subject, which makes it is possible to generate representative data that can be used to train other models (e.g. machine learning based algorithms).

Generally, in one aspect, a method implemented using one or more processors may include: applying one or more simulation parameters to a digital twin created for a subject, wherein the digital twin simulates an anatomical structure of the subject, and wherein the one or more simulation parameters cause the digital twin to generate digital twin output that simulates behavior of the anatomical structure in response to the one or more simulation parameters; applying data indicative of the digital twin output as input across a pain estimation machine learning model to generate pain estimation output, wherein the pain estimation machine learning model is trained to estimate a quantification of pain that the subject would experience based on application of the simulation parameters, and wherein the pain estimation output indicates the quantification of pain; and based on the pain estimation output, rendering the quantification of pain using an output device or selecting a treatment plan.

In various embodiments, the pain estimation machine learning model comprises a convolutional neural network. In various embodiments, the anatomical structure comprises a heart of the subject, and the digital twin output comprises an electrocardiogram ("ECG") signal. In various embodiments, the one or more simulation parameters comprise a physical or daily activity. In various embodiments, the one or more simulation parameters comprise a medication or therapy.

In various embodiments, the method may further include comparing the digital twin output to one or more additional outputs of one or more healthy digital twins to determine at least one digital twin delta, wherein each of the one or more healthy digital twins simulates an anatomical structure in a different healthy subject, and wherein the data indicative of the digital twin output comprises the at least one digital twin delta. In various embodiments, the one or more additional outputs of one or more healthy twins comprise a plurality of additional outputs of a plurality of healthy digital twins, the at least one digital twin delta comprises a plurality of digital twin deltas, and the data indicative of the digital twin output comprises a value calculated based on the plurality of digital twin deltas.

In various embodiments, additional output of a first healthy digital twin of the plurality of healthy digital twins is weighted more heavily than a second additional output of a second healthy digital twin of the plurality of healthy digital twins based on one or more criteria. In various embodiments, the one or more criteria include a healthy subject underlying the first healthy digital twin having a greater measure of similarity to the subject than another healthy subject underlying the second healthy digital twin.

In another aspect, a method of training a pain estimation machine learning model may include: providing a first set of digital twins to simulate an anatomical structure in a plurality of pained subjects; determining pain scores observed by the plurality of pained subjects; applying one or more simulation parameters to each digital twin of the first set to generate a plurality of digital twin outputs, wherein each digital twin output simulates behavior of the anatomical structure in a respective subject of the first set in response to the one or more simulation parameters; applying data indicative of the plurality of digital twin outputs as inputs across a pain estimation machine learning model to generate pain estimation outputs; and training the machine learning model based on comparison of the pain estimation outputs to the pain scores.

In various embodiments, the method may further include: providing a second set of digital twins to simulate the anatomical structure in a plurality of pain-free subjects; and applying the one or more simulation parameters to each digital twin of the second set to generate additional digital twin outputs, wherein each additional digital twin output simulates behavior of the anatomical structure in a respective subject of the second set in response to the one or more simulation parameters.

In various embodiments, the method may further include comparing the additional digital twin outputs to the plurality of digital twin outputs generated from the first set of digital twins to determine a plurality of digital twin deltas, wherein the data indicative of the plurality of digital twin outputs comprises the plurality of digital twin deltas.

In various embodiments, the method may further include: determining additional pain scores associated with the plurality of pain-free subjects; applying data indicative of the additional digital twin outputs as inputs across the pain estimation machine learning model to generate additional pain estimation outputs; and training the machine learning model based on comparison of the additional pain estimation outputs to the additional pain scores. In various embodiments, determining the additional pain scores associated with the plurality of pain-free patients includes setting each of the additional pain scores to a control value.

In addition, some implementations include one or more processors of one or more computing devices, where the one or more processors are operable to execute instructions stored in associated memory, and where the instructions are configured to cause performance of any of the aforementioned methods. Some implementations also include one or more non-transitory computer readable storage media storing computer instructions executable by one or more processors to perform any of the aforementioned methods.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

BRIEF DESCRIPTION OF THE DRAWINGS

In the drawings, like reference characters generally refer to the same parts throughout the different views. Also, the drawings are not necessarily to scale, emphasis instead generally being placed upon illustrating various principles of the embodiments described herein.

DETAILED DESCRIPTION

Pain quantification is a difficult problem because pain is generally a subjective observation. Attempts have been made to analyze physiological signals to predict a subject's experience of pain. For example, the firing of spinal cord neurons has been used to attempt to quantify a measure of pain experienced by a subject. However, these techniques do not facilitate estimation of pain that a subject will experience if the subject is treated with a given therapy.

In view of the foregoing, various embodiments and implementations of the present disclosure are directed to quantification and estimation, e.g., of pain scores or other subjective or hard-to-calculate metrics, using digital twin output. For example, in various embodiments, outputs of a biophysical model (e.g., a digital twin) of an anatomical structure or system may be analyzed to train machine learning model(s) to estimate a quantified amount of pain a subject is likely to experience, given application of particular stimuli to the biophysical model.

Figure 1:
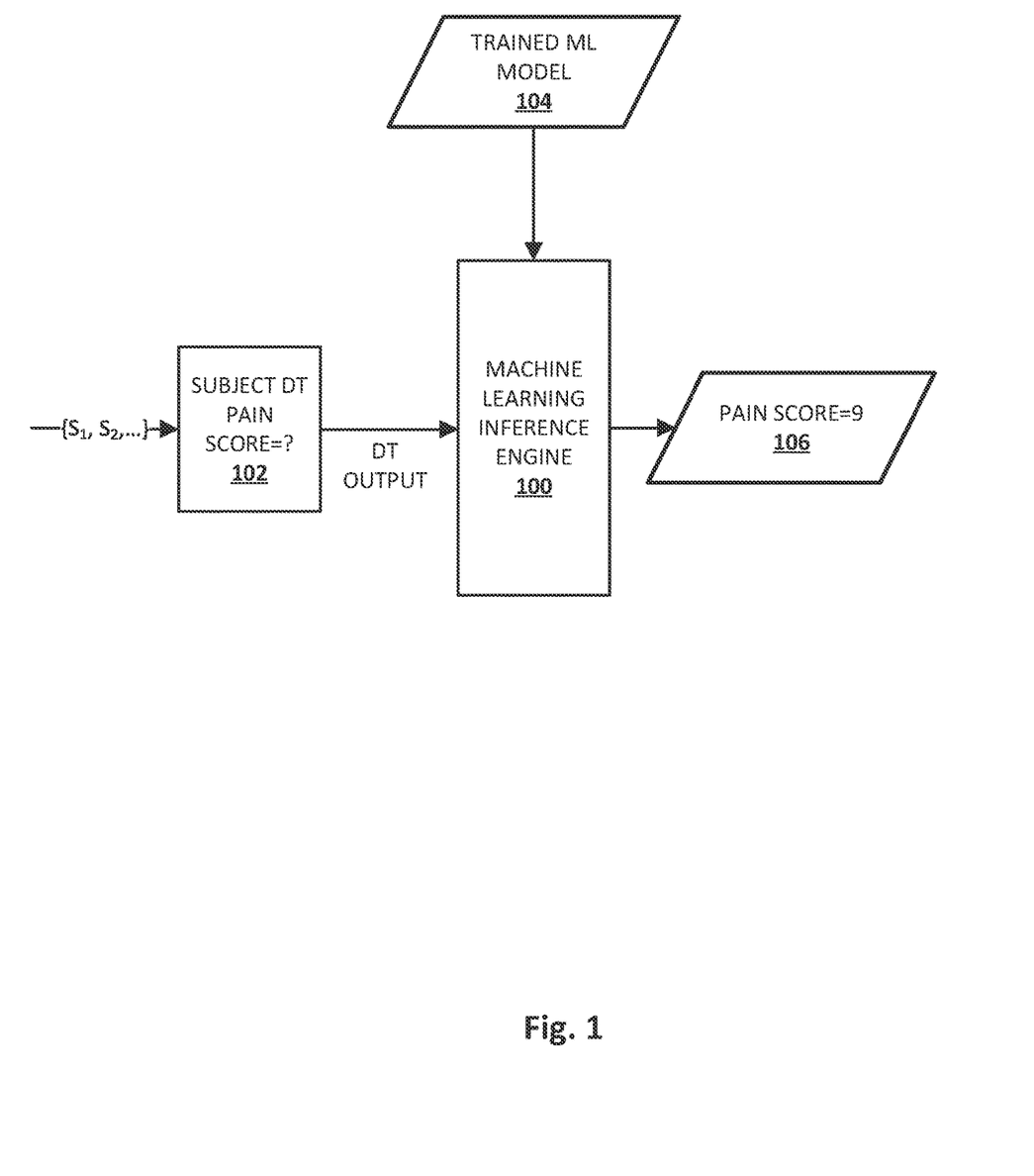
FIG. 1 schematically illustrates a first example of how techniques described herein may be implemented to estimate a quantification of pain, in accordance with various embodiments.

FIG. 1 schematically depicts on example of how a trained "pain estimation" machine learning model 104 may be applied to estimate a pain quantification 106 (also referred to as an "estimated pain score"). In FIG. 1, a machine learning inference engine 100 may be implemented by one or more computing devices using any combination of hardware and computer-readable instructions (e.g., software) stored in a transitory or non-transitory medium. Computing devices described herein may include, for example, one or more of: a desktop computing device, a laptop computing device, a tablet computing device, a mobile phone computing device, a computing device of a vehicle of the user (e.g., an in-vehicle communications system, an in-vehicle entertainment system, an in-vehicle navigation system), a standalone interactive speaker (which in some cases may include a vision sensor), a smart appliance such as a smart television (or a standard television equipped with a networked dongle with automated assistant capabilities), and/or a wearable apparatus of the user that includes a computing device (e.g., a watch of the user having a computing device, glasses of the user having a computing device, a virtual or augmented reality computing device). Additional and/or alternative computing devices may be provided.

Also depicted in FIG. 1 is a biology-driven (and/or anatomy-driven) model that is referred to herein as a "digital twin" ("DT" in several of the FIG. 102 to avoid confusion with machine learning models described herein, such as pain estimation machine learning model 104. A "digital twin" 102 (or digital "avatar") is a digital replica of a living or non-living physical entity. In the context of the present disclosure, a "digital twin" may be created to simulate one or more anatomical structures of a human or non-human subject, such as one or more internal organs and/or one or more physiological systems, all the way up to an entire subject (i.e., a "virtual patient"). In FIG. 1, digital twin 102 corresponds to a subject, such as a patient, for which it is desired to generate an estimated pain quantification 106. A "physiological system" may include, but is not limited to, the respiratory system, endocrine system, digestive system, urinary system, lymphatic system, skeletal system, cardiovascular system, integumentary system, nervous system, muscular system, and reproductive system, to name a few.

Various simulation parameters $\{S1, S2, \ldots\}$ can be applied and/or input to a digital twin 102 to cause digital twin 102 to generate output ("DT OUTPUT" in FIG. 1) that simulates behavior of the digital twin's real-world counterpart. Simulation parameters $\{S1, S2, \ldots\}$ may be designed to simulate real-world parameters that might be applied to a subject and/or to anatomical structure(s) within the subject, with the goal of simulating a physical and/or behavioral response of the subject without actually applying the real-world parameters to the actual subject. In various embodiments, simulation parameters {S1, S2, . . . } may include simulated administration of medicine (e.g., type, dosage, conditions under which it is administered), simulated application of therapy (e.g., physical therapy, implants and/or prosthetics, organ transplants, etc.), simulated activity (e.g., exercise and/or stretching prescribed by a clinician), simulated nutritional intake (e.g., high protein, low carb diet, etc.), daily activities (e.g., urination), and so forth.

The output of digital twin 102 may take various forms corresponding to various physiological and/or symptomatic responses of digital twin 102 to the input simulation parameters {S1, S2, . . . }. In some embodiments, the number of outputs may correspond to the number of inputs (e.g., simulation parameters), although this is not required. Examples of physiological responses that may be represented by output of digital twin 102 include, for instance, heart rate, temperature, respiration rate, insulin response, glucose levels, blood oxygen levels, and so forth. In various implementations, output of digital twin 102 may include simulated electrocardiogram ("ECG") signal(s), one or more simulated signals indicative of blood oxygen levels or saturation (e.g., $SpO_2$), etc. Symptomatic responses of digital twin 102 (which may be indicated and/or conveyed by output of digital twin 102) may include, for instance, restlessness, hunger, anxiety, thirst, drowsiness, itching, pain, etc.

Digital twin 102 may be constructed in various ways. In some embodiments, digital twin 102 may include one or more (e.g., an ensemble of) constituent functions that collectively calculate and generate, alone or collectively with other constituent functions, output that is indicative of how the real-world counterpart of the anatomical structure simulated by digital twin 102 would behave under certain conditions (e.g., simulation parameters). These constituent functions may take various forms, such as heuristics, statistical models, causal graphs such as causal Bayesian networks and/or probabilistic graphical models, trained machine learning models (e.g., neural networks), decision trees, support vector machines, and so forth. Various inputs (e.g., simulation parameters) may be applied to various portions of digital twin 102, such as inputs of any of these constituent functions. These inputs may simulate various activities and/or measurements. For example, simulation parameters could include calculated and/or measured subject data, such as physiological attributes (e.g., heart rate, blood pressure, hemodynamic instability), medical images (e.g., ultrasound images, CT scans), and/or other medical and/or subject data.

Machine learning inference engine 100 may be configured to apply trained pain estimation machine learning model 104 across various inputs to generate pain estimation output that is indicative of pain a subject would experience based on application of simulation parameters. This pain estimation output may include or convey a pain quantification estimate 106 that assigns a quantitative value-such as a number between zero and ten or a relative value with respect to a different subject—to the amount of pain conveyed in the pain estimation output. Pain estimation machine learning model 104 may take various forms, such as a support vector machine, a decision tree, a random forest, a neural network, etc. In some embodiments, pain estimation machine learning model 104 may take the form of a feed-forward or convolutional neural network, a recurrent neural network (e.g., where output of digital twin 102 is a sequence), and so forth.

Figure 2:
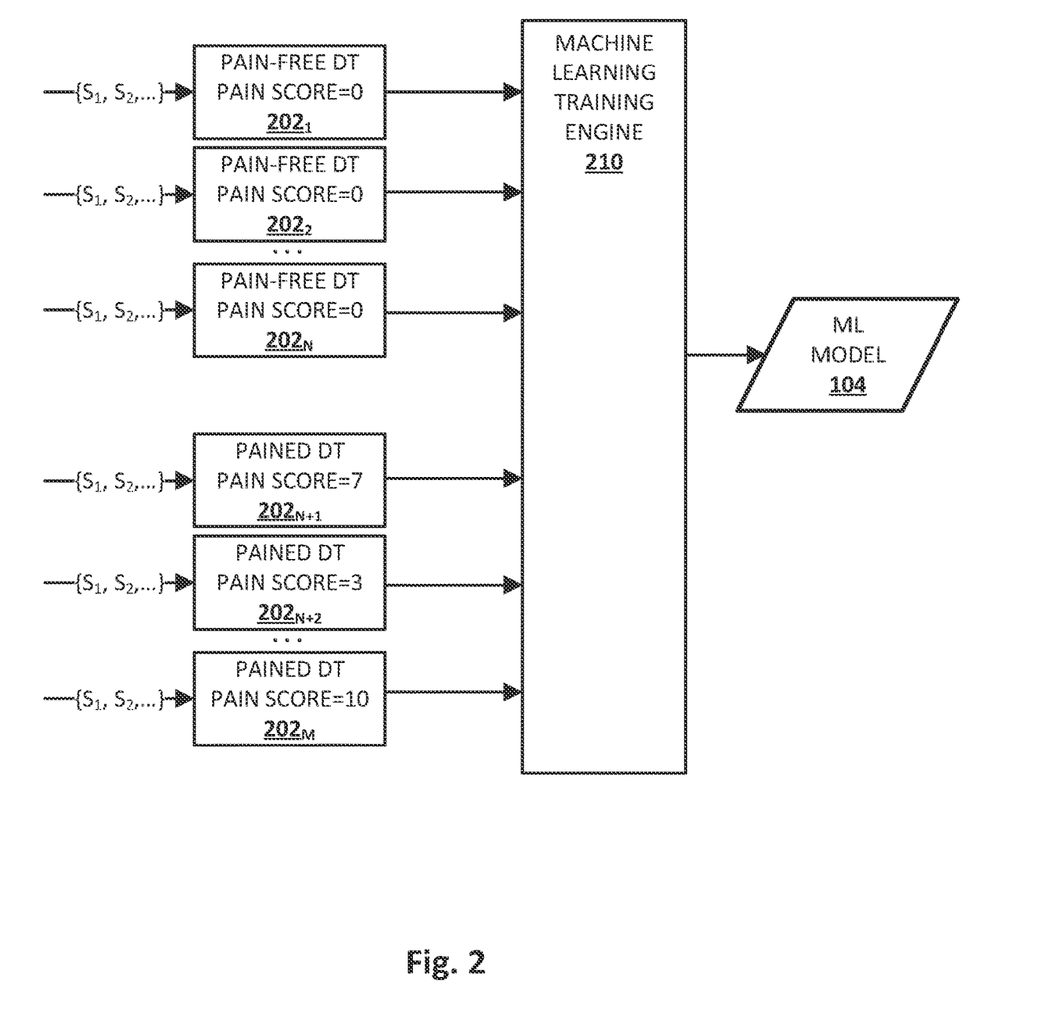
FIG. 2 schematically illustrates a first example of how techniques described herein may be implemented to train a pain estimation machine learning model, in accordance with various embodiments.

FIG. 2 depicts one example of how pain estimation machine learning model 104 may be trained, e.g., by a machine learning training engine 210. Machine learning training engine 210 may be implemented on one or more computing devices using any combination of hardware and computer-readable instructions that are executable by one or more processors. In FIG. 2, training data takes the form of outputs from a plurality of digital twins, $202_{1-M}$. These digital twins may correspond to the same anatomical structure across multiple different subjects. Each digital twin 202 is associated with ground truth data in the form of a known, observed and/or ranked pain score.

A first set of digital twins $202_{1-N}$ simulate the anatomical structure in a plurality of "pain-free," "healthy," or "control" subjects. In some embodiments, observed pain scores of first set of digital twins $202_{1-N}$ may be set to zero or to some other value. These pain-free digital twins $202_{1-N}$ may be akin to a control group that provides a necessarily objective (and/or validated/verified) measurement of pain.

A second set of digital twins $202_{N+1}$ to M simulates the anatomical structure in a plurality of "pained," "unhealthy," or "maligned" subjects. This known pain score may have been observed by the subject whose anatomical structure is simulated by the respective digital twin 202 of the second set. In FIG. 2 and elsewhere herein, pain scores are integers that lie in a range of one to ten, but this is not meant to be limiting. Non-integers and even non-numbers (e.g., grades such as A-F) may be used as pain scores. As an example, the subject for which first pained digital twin $202_{N+1}$ was created reported a pain score of seven. The subject for which second pained digital twin $202_{N+2}$ was created reported a pain score of three. And the subject for which the Mth digital twin $202_M$ was created reported a pain score of ten.

One or more simulation parameters {S1, S2, . . . } may be applied/input to each digital twin $202_{1-M}$ to generate a plurality of digital twin outputs. These simulation parameters may be selected in various ways based on various criteria. For example, simulation parameters that are known to have been provided to the subjects for which digital twins $202_{1-M}$ were created in order to generate the reported pain scores may be used. In some cases, a union of simulation parameters applied to both sets of subjects may be selected. Additionally or alternatively, simulation parameters may be selected that are likely to yield large discrepancies in reported pain and/or digital twin output between the pain-free and pained subjects corresponding to, respectively, digital twins $202_{1-N}$ and $202_{N+1}$ to M.

Once a plurality of digital twin outputs are generated, data indicative of these outputs may be applied, e.g., by machine learning training engine 210 as inputs across pain estimation machine learning model 104 to generate pain estimation outputs. This may be performed individually or in batches. Machine learning training engine 210 may train pain estimation machine learning model 104 based on a comparison of the pain estimation outputs to the known/observed pain scores. For example, any difference, or error, between an estimated pain output and the known pain score may be used to perform techniques such as back propagation and/or gradient descent to update weights of pain estimation machine learning model 104. Pain estimation machine learning model 104 may then be used, e.g., by machine learning inference engine 100 as described previously, to estimate pain that would be experienced by a subject if particular simulation parameters (e.g., their real-world counterparts) were applied to the subject.

Rather than estimating pain quantification based on individual digital twin output, as was the case in FIG. 1, in some embodiments, pain quantification may be estimated (and the underlying pain estimation model 104 may be trained) based on differences between pairs of digital twins. This may facilitate more accurate estimation of the relative and/or subjective nature of pain. An example of such an embodiment is depicted in FIG. 3 (inference) and FIG. 4 (training).

Figure 3:
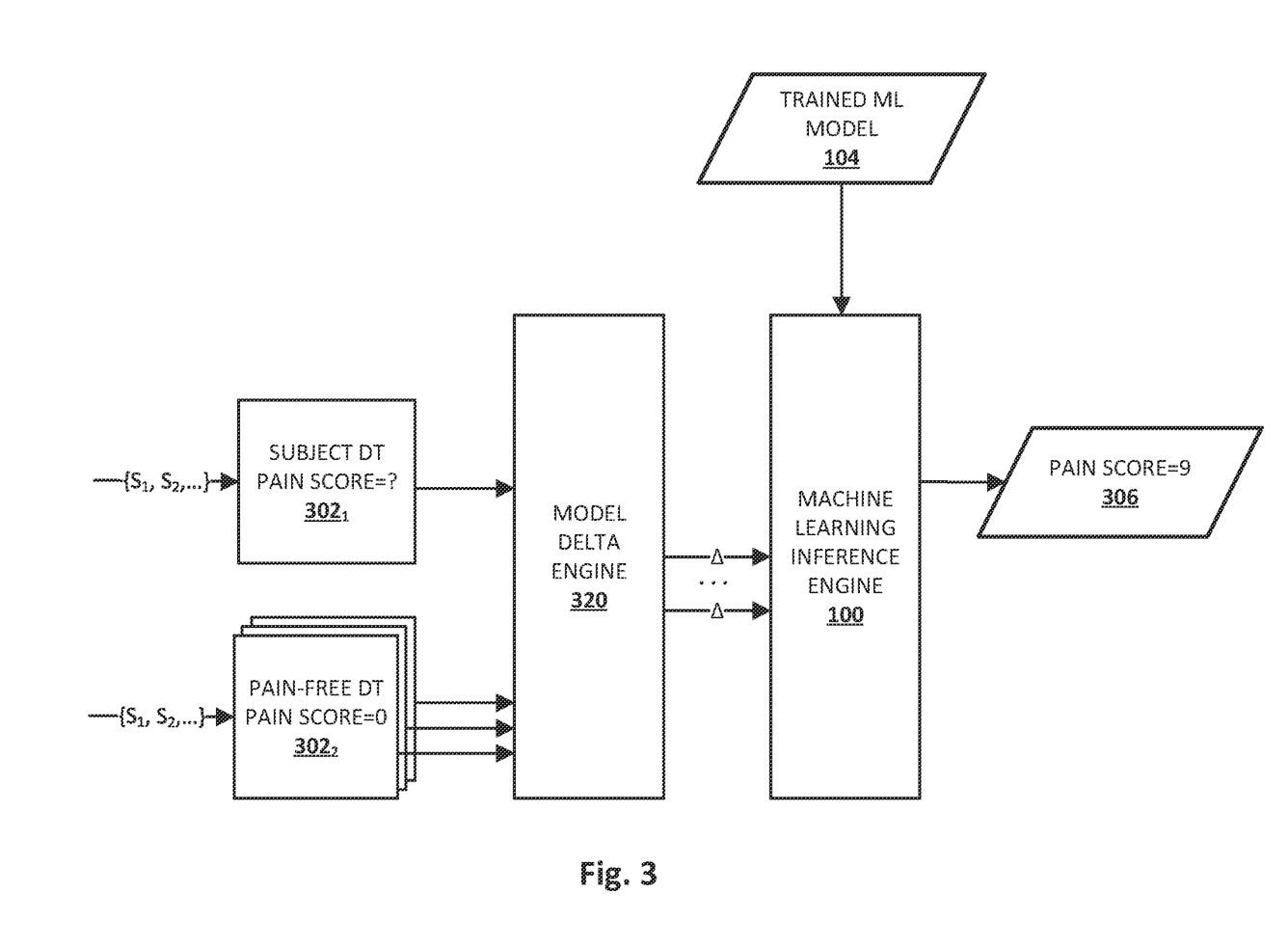
FIG. 3 schematically illustrates a second example of how techniques described herein may be implemented to estimate a quantification of pain, in accordance with various embodiments.

FIG. 3 is similar to FIG. 1 except that in FIG. 3, a model delta engine 320 is provided that calculates differences or "deltas" between pairs of digital twin models. As with other components described herein, model delta engine 320 may be implemented on one or more computing devices using any combination of hardware and computer-readable instructions that are executable by one or more processors. As one non-limiting example of a digital twin delta, a first ECG signal generated by one digital twin may be subtracted from a second ECG signal generated by another digital twin (e.g., after preprocessing of the signals for alignment and/or filtering) to yield a delta ECG signal. As another example, feature(s) extracted from the first ECG signal may be compared to corresponding feature(s) extracted from the second ECG signal to calculate a feature delta. In other words, a delta can be considered as a function of the ECG signals or as a function of features extracted from the ECG signals.

In this example, the "subject" digital twin $302_1$ is once again created to simulate an anatomical structure of a subject (e.g., a patient) of interest. Also provided are a pool of one or more additional digital twins $302_2$, that are generated to simulate the same anatomical structure across one or more pain-free or healthy subjects. The same simulation parameters {S1, S2, ... } may be applied/input to all digital twins 302 to cause digital twins 302 to generate respective digital twin outputs. These outputs may be processed by model delta engine 320 to generate one or more digital twin deltas (each signified by a "Δ" in FIG. 3) that represent differences between the subject of interest (for which digital twin $302_1$ was created) and pain-free subjects (for which digital twins $302_{2-?}$ were created).

The digital twin deltas may be generated by model delta engine 320 in various ways. In some embodiments, a digital twin delta may be calculated between the pain digital twin $302_1$ and each of the pain-free digital twins $302_{2-?}$. Then, a pain score or quantification 306 may be estimated for each of these deltas, e.g., by machine learning inference engine 100 using trained pain estimation machine learning model 104. In some embodiments, a final pain score estimation 306 may be calculated, e.g., by machine learning inference engine 100, as a mean or median of the pain scores calculated for the deltas.

Figure 4:
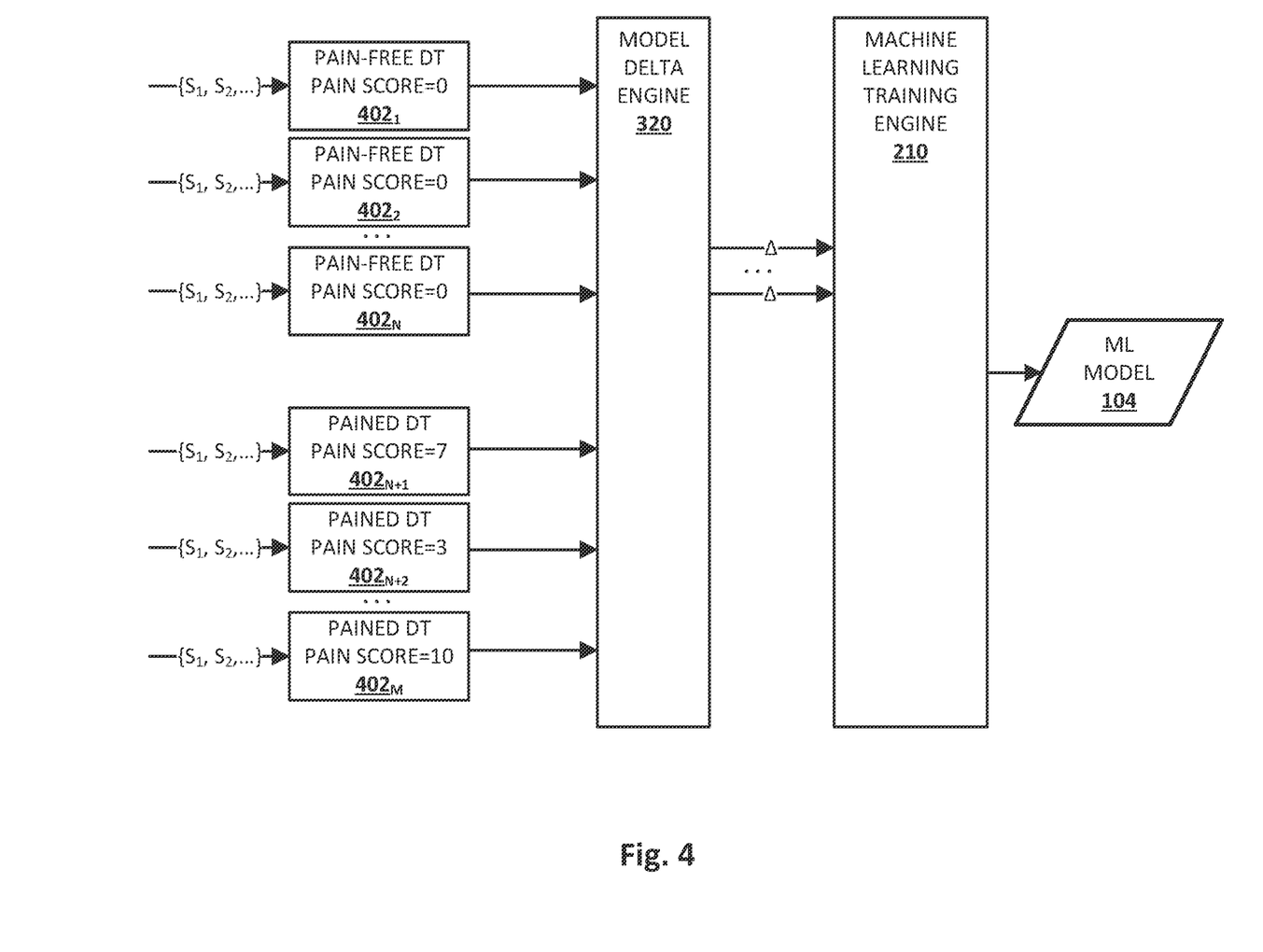
FIG. 4 schematically illustrates a second example of how techniques described herein may be implemented to train a pain estimation machine learning model, in accordance with various embodiments.

FIG. 4 schematically illustrates one example of how techniques described herein may be implemented to train pain estimation machine learning model 104 so that it can be applied as shown in FIG. 3. In FIG. 4, a first set of pain-free digital twins $402_{1-N}$ and a second set of pained digital twins $402_{N+1}$ to M are provided, similar as in FIG. 2. As was the case in FIG. 3, each pained digital twin of the second set ($402_{N+1}$ to M) is compared by model delta engine 320 to each pain-free (or healthy) digital twin of the first set ($402_{1-N}$) to generate a respective digital twin delta. Additionally, a digital twin delta may be calculated between each pair of the first set of pain-free digital twins $402_{1-N}$. In other words, if there are ten pain-free digital twins ($402_{1-10}$) in the first set and two subject digital twin ($402_{11-12}$) in the second set, then twenty (pained, pain-free) deltas would be computed and forty-five (pain-free, pain-free) deltas would be computed.

Similar to FIG. 3, in FIG. 4, machine learning training engine 210 may apply the digital twin deltas generated by model delta engine 320 as input across the pain estimation machine learning model 104 to generate pain estimation outputs. These pain estimation outputs may be compared to corresponding reported/observed pain scores associated with the subjects for which anatomical structures are simulated by digital twins $402_{1-M}$. Based on those comparisons, machine learning training engine 210 may train pain estimation machine learning model 104, e.g., using techniques such as gradient descent, back propagation, etc.

Figure 5:
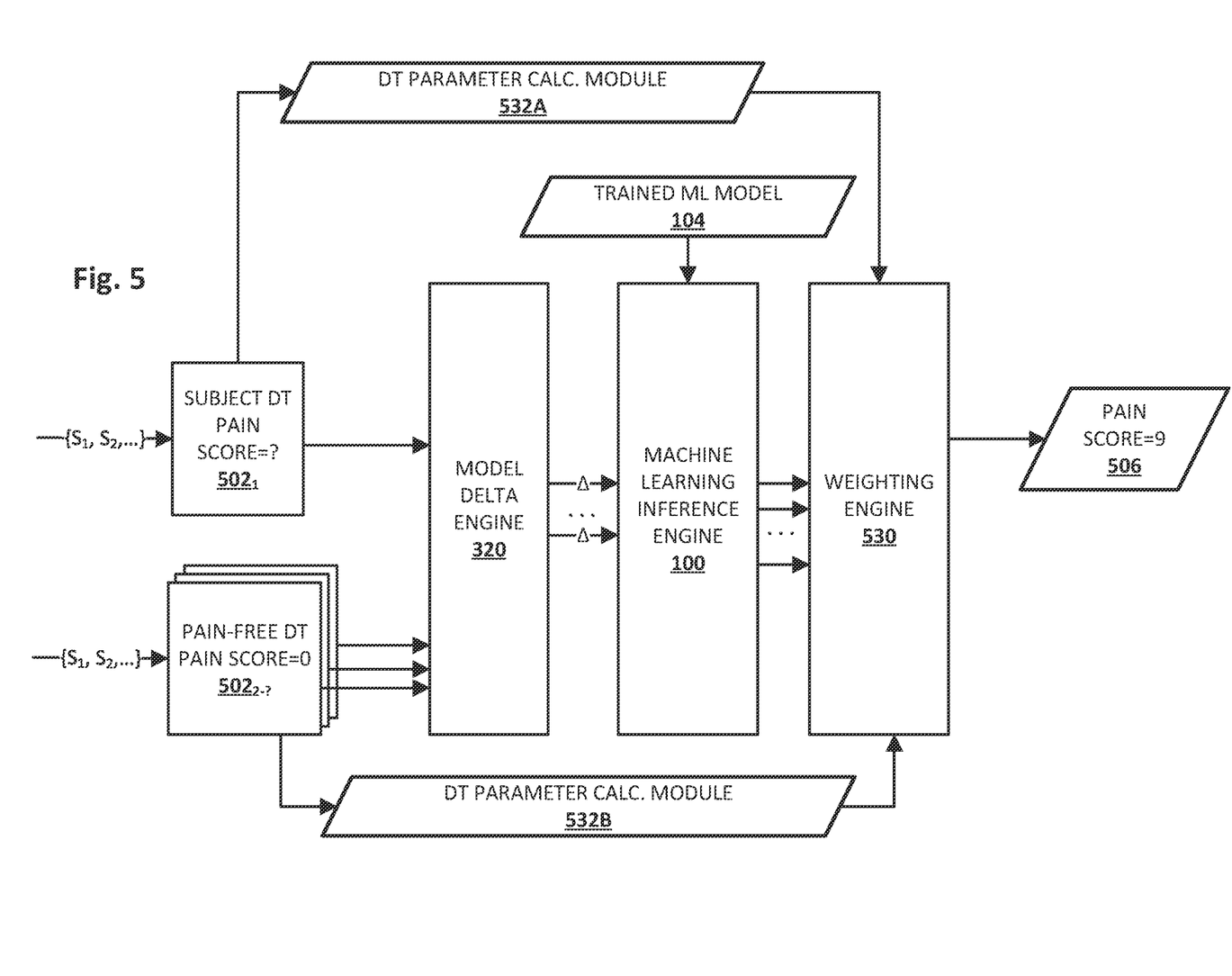
FIG. 5 schematically illustrates a third example of how techniques described herein may be implemented to estimate a quantification of pain, in accordance with various embodiments.

FIG. 5 shows one additional example of how techniques described here can be employed to estimate a pain score 506 of a subject simulated at least in part by a subject digital twin $502_1$. Any many respects, FIG. 5 is similar to FIG. 3 in that one or more aspects (e.g., digital twin output) of a subject digital twin $502_1$ created for a subject-of-interest (e.g., a patient being examined) is compared, e.g., by model delta engine 320, to a pool of pain-free digital twin models $502_2$; to generate a plurality of respective deltas. These deltas are applied, e.g., by machine learning inference engine 100, as inputs across trained pain estimation machine learning model 104 to generate respective outputs. In FIG. 3 these outputs comprised pain score estimations from which a final pain score was tallied. By contrast, in FIG. 5, these outputs are preliminary. In particular, the outputs of machine learning inference engine 100 are processed by a weighting engine 530 to determine a final estimated pain score.

Weighting engine 530 may be implemented by one or more computing devices using any combination of hardware and computer-readable instructions that are executable by one or more processors. Weighting engine 530 may be configured to weight the various outputs it receives from machine learning inference engine 100 based on a variety of factors. Some of these factors may include characteristics associated with the underlying digital twins $502_1$, that generated the digital twin outputs from which the pain estimation outputs were determined. These characteristics may be analyzed by digital twin parameter calculation modules 532A and 532B. Digital twin parameter calculation modules 532A and 532B may be implemented by one or more computing devices using any combination of hardware and computer-readable instructions that are executable by one or more processors. Although depicted separately in FIG. 5, in some embodiments, they may be implemented as a single module, and in some cases may be incorporated with and/or integral parts of weighting engine 530.

Digital twin parameter calculate modules 532A and 532B may be configured to analyze various parameters and/or characteristics of digital twins-particularly from the pool of pain-free digital twins $502_{2-?}$—to determine which pain estimation outputs should be weighted more or less heavily than others by weighting engine 530. For example, some of pain-free digital twins $502_2$; may be deemed more accurate than others, e.g., because more accurate and/or extensive medical information is available about the underlying subjects. Pain estimation outputs generated based on deltas between these more accurate pain free digital twins and the subject digital twin $502_1$ may be assigned relatively greater weights than other pain estimation outputs.

Digital twin parameter calculate modules 532A and 532B may consider a variety of characteristics of digital twins to determine, for instance, digital twin accuracies that can be used by weighting engine 530 to assign weights to pain estimation outputs. For example, metadata associated with a digital twin may explicitly indicate a measure of accuracy of the digital twin, or may convey some other attribute of the digital twin and/or the underlying subject that is probative of greater accuracy, such as a number of tests run on the subject, a period of time over which the subject has been a patient, a frequency at which the subject visited a clinician, etc.

In some embodiments, one or more limitations of a digital twin 502, conveyed in metadata or identified by digital twin calculation module 532, may be used as a factor in weighting the pain estimation output generated using the output of that digital twin. For example, the digital twin may lack a particular anatomical measurement or feature of a larger anatomical structure (e.g., because information about that anatomical measurement/feature for the subject is unavailable), whereas other digital twins may include that particular anatomical measurement/feature. Another limitation may be, for instance, that the digital twin 502 being analyzed (or the underlying subject in real life) has not been previously subjected to the same simulation parameters that are being applied across all the digital twins $502_{1-?}$.

In some embodiments, the training data that was used to generate a digital twin 502 may be considered, e.g., by weighting engine 530, in-and-of-itself and/or as an indicator of overall digital twin accuracy. As alluded to above, the more medical information available about a subject underlying the digital twin 502, the more accurate the digital twin 502 will likely be. The extensiveness (and/or accuracy) of this underlying medical data may be manifested in training data that is used to train and/or create various aspects of the digital twin 520. Generally speaking, the more training data, the more accurate the model.

In addition to or instead of the training data, an algorithm that was used to train one or more aspects of the digital twin model may also be considered. For example, if a digital twin includes a trained machine learning model (not to be confused with pain estimation machine learning model 104), that model may have been trained using one algorithm that, for various reasons, may have yielded a more accurate model than an algorithm used to generate similar aspects of the another digital twin. This may be taken into account by weighting engine 530 when calculating the final estimated pain score 506.

In some implementations, a subset of the pain-free digital twins $502_2$; may be weighted more heavily than other pain-free digital twins because the underlying subjects are known to be more similar to the subject-of-interest for which subject digital twin $502_1$ was created. This "similarity" may be determined, e.g., by digital twin parameter calculation module 532 and/or weighting engine 530, in various ways. Physiological similarity may be found or heightened where, for instance, pain-free subjects have similar vital signs, physiological characteristics (e.g., weight, height, gender), medical histories (e.g., similar number/type of past surgeries, similar past diagnosis of various diseases), etc., with the subject-of-interest Additionally or alternatively, demographic and/or environmental similarity may be considered in some embodiments. For example, two nearby subjects may have been exposed to similar pollution levels.

Figure 6:
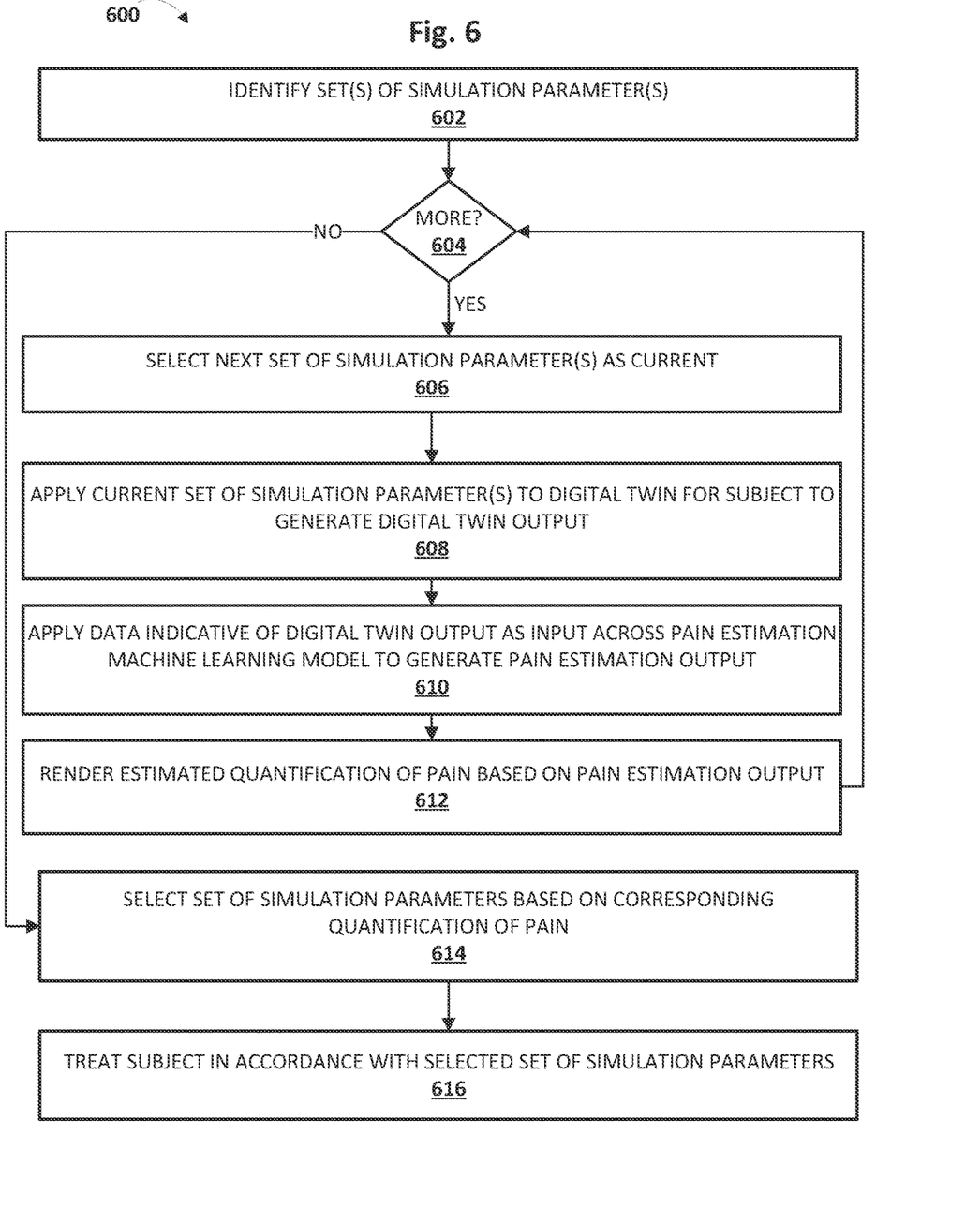
FIG. 6 depicts a method for practicing selected aspects of the present disclosure.

FIG. 6 illustrates a flowchart of an example method 600 for practicing selected aspects of the present disclosure. The steps of FIG. 6 can be performed by one or more processors, such as one or more processors of the various computing devices/systems described herein. For convenience, operations of method 600 will be described as being performed by a system configured with selected aspects of the present disclosure. This system may be operated, for instance, by a clinician that is treating a subject-of-interest, or patient. For example, the clinician may be considering multiple different treatment plans for the patient, and may wish to estimate the relative amounts of pain the patient will experience with each treatment plan. Other implementations may include additional steps than those illustrated in FIG. 6, may perform step(s) of FIG. 6 in a different order and/or in parallel, and/or may omit one or more of the steps of FIG. 6.

At block 602, the system may identify one or more sets of simulation parameters. Each set of these one or more sets of simulation parameters may include for instance, one or more actions that may be taken as part of a treatment plan for the patient. These actions may include, for instance, administration of medicine, performance and/or prescription of various types of therapies, prescription of activity such as exercise or stretching, prescription of a particular nutritional plan, or any other action may be considered as part of a treatment plan for the patient. As one example, for a patient experiencing chronic pain, one particularly aggressive treatment plan may include surgery (which usually involves administration of various medicines such as anesthetics) coupled with physical therapy. Another somewhat less aggressive treatment plan may include administration of a relatively strong pain medication (e.g., prescription only) coupled with some sort of physical therapy. An even less aggressive treatment plan may include recommendation that the patient take an over-the-counter pain medicine coupled with exercise. Within each of these treatment plans, each action or recommendation may comprise a simulation parameter, and consequently, each treatment plan may comprise a set of simulation parameters.

At block 604, the system may determine whether there are more sets of simulation parameters (e.g., treatment options or plans) to consider. If the answer is yes, then method 600 may proceed to block 606. At block 606, the system may select a next set of simulation parameters as a current set.

At block 608, the system may apply and/or input the current set of simulation parameters to a digital twin created for the subject-of-interest to generate digital twin output. How these simulation parameters are applied depends on the parameters themselves, as well as the structure of the digital twin, e.g., what inputs the digital twin has available. The digital twin outputs can take various forms as well, as described previously. As one non-limiting example, one or more simulation parameters may cause the digital twin to generate output in the form of one or more ECG signals.

At block 610, the system, e.g., by way of machine learning inference engine 100 (or machine learning training engine 210 if during training), may apply data indicative of the digital twin output as input across a pain estimation machine learning model (e.g., 104) to generate pain estimation output. The data indicative of the digital twin output may include the digital twin output verbatim and/or feature(s) extracted from the digital twin output. For example, tens or even hundreds of features may be extracted from a simulated ECG signal contained in digital twin output and applied as inputs across a pain estimation machine learning model such as a convolutional neural network.

In some embodiments, at block 612, the system may render an estimation quantification of pain (e.g., an estimated pain score) based on the pain estimation output generated during block 610. This output may be rendered visually on a screen, audibly, etc. The rendered output may be used by the clinician to understand how much pain a given treatment plan is likely to cause the patient. This may enable the clinician to perform a risk/rewards analysis. If the treatment plan is likely to be highly effective (medically and/or financially), the clinician and/or patient may be willing to tolerate the patient experiencing more pain than might be the case for a less effective and/or more expensive treatment plan. Alternatively, the rendered output may be used to help a clinician better account for quality of life factors while making treatment decisions.

Method 600 may then return to block 604 to determine whether there are additional sets of simulation parameters to be considered. If the answer is yes, then blocks 606-612 are repeated for the next set of simulation parameters. However, if the answer at block 604 is no, then method 600 may proceed to block 614. At block 614, the system may select a set of simulation parameters based on the corresponding estimated quantification of pain (e.g., estimated pain score) generated from that set of simulation parameters. For example, if three treatment plans (i.e., three sets of simulation parameters) are under consideration, and assuming all three are equally likely to be similarly effective, the treatment plan having the lowest estimated pain score may be selected, e.g., to be rendered on a display as the best treatment plan.

At block 616, the patient may be treated in accordance with the treatment plan represented by the set of simulation parameters selected at block 614. In some implementations, this may involve the clinician (and other medical personnel where applicable) treating the patient (prescribing, administering) in accordance with the treatment plan. In other implementations, techniques described herein could be applied by medical equipment to automatically (e.g., without human intervention) select a best treatment option of multiple treatment options capable of being applied by the medical equipment.

For example, a piece of medical equipment may have at its disposal multiple different medicines that treat similar symptoms. The medical equipment—or a computing system such as a hospital information system ("HIS") communicative coupled with the medical equipment—may automatically select and administer the medicine that is likely to cause the patient the least amount of pain. As another example, a computing device (e.g., server(s) in the cloud) may be configured to select from a plurality of exercise and/or nutrition plans for a patient. That computing device may practice selected aspects of the present disclosure to estimate pain and/or other discomfort that will be caused to the patient by each of these exercise/nutrition plans. Based on those estimated pain scores, the computing device may select and cause to be recommended—e.g., at a client device operated by the patient such as a smart phone, smart watch, tablet, smart glasses, etc.—the exercise/nutrition plan likely to cause the patient the least pain or discomfort.

Figure 7:
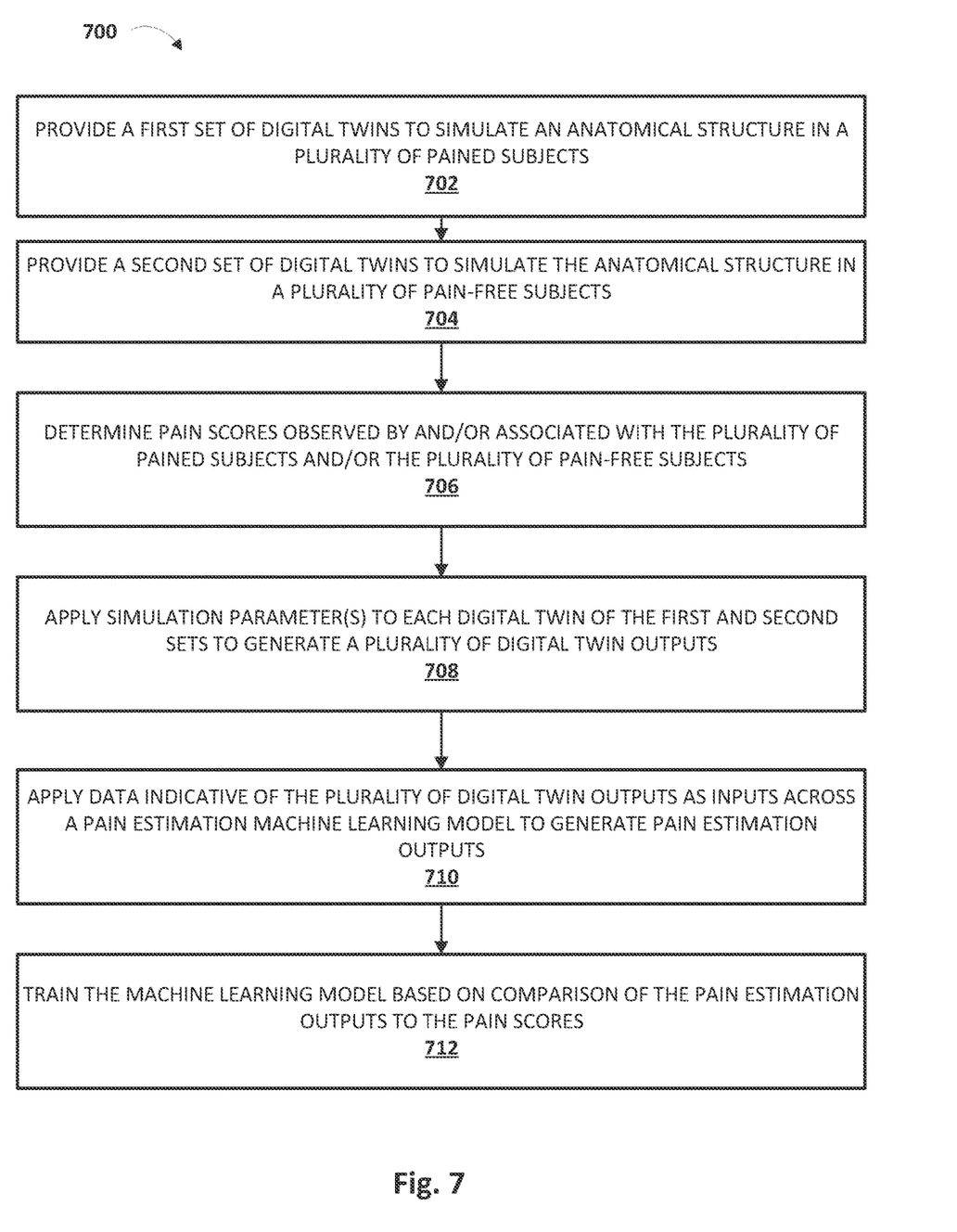
FIG. 7 depicts a method for practicing selected aspects of the present disclosure.

FIG. 7 illustrates a flowchart of an example method 700 for practicing selected aspects of the present disclosure to train a pain estimation machine learning model. The steps of FIG. 7 can be performed by one or more processors, such as one or more processors of the various computing devices/systems described herein. For convenience, operations of method 700 will be described as being performed by a system configured with selected aspects of the present disclosure, such as machine learning training engine 210. Other implementations may include additional steps than those illustrated in FIG. 7, may perform step(s) of FIG. 7 in a different order and/or in parallel, and/or may omit one or more of the steps of FIG. 7.

At block 702, the system may provide (e.g., retrieve and/or generate from data hosted in an HIS) a first set of digital twins to simulate an anatomical structure in a plurality of pained subjects. Examples of such a first set were shown in FIG. 2 at $202_{N+1}$ to $202_M$, and in FIG. 4 at $402_{N+1}$ to $402_M$. At block 704, the system may provide a second set of digital twins to simulate the anatomical structure in a plurality of pain-free subjects. Examples of such a second set were shown in FIG. 2 at $202_{1-N}$ and in FIG. 4 at $402_{1-N}$.

At block 706, the system may determine pain scores observed by and/or associated with the plurality of pained subjects and/or the plurality of pain-free subjects. With pained subjects these scores may be self-reported. With pain-free or healthy subjects these pain scores may be set automatically (e.g., to zero) or self-reported. Pain scores for healthy/pain-free subjects need are not limited to zero, and some healthy subjects may in fact experience some pain. Rather, the healthy subjects are used herein as a control group to which comparisons can be drawn, in order to facilitate estimation of a subjective metric such as a pain score.

At block 708, the system may apply simulation parameter(s) to each digital twin of the first and second sets to generate a plurality of digital twin outputs. Each digital twin output may simulate behavior of the anatomical structure in a respective subject of the first or second set in response to the one or more simulation parameters.

At block 710, the system may apply data indicative of the plurality of digital twin outputs as inputs across a pain estimation machine learning model to generate pain estimation outputs. As noted previously, the data indicative of the plurality of digital twin outputs may be the digital twin outputs themselves or deltas generated based on the digital twin outputs. For example, in some embodiments, the system may compare digital twin outputs generated from the first set of digital twins with digital twin outputs generated from the second set of digital twins to determine a plurality of digital twin deltas. In some cases, the system may also compare pairs of digital twin outputs from the second set to generate additional deltas. In some such embodiments, these deltas may be applied as input across the pain estimation machine learning model.

At block 712, the system may train the machine learning model based on comparison of the pain estimation outputs to the pain scores. As noted previously, training techniques such as back propagation and/or gradient descent (e.g., stochastic gradient descent) may be applied in some embodiments.

Figure 8:
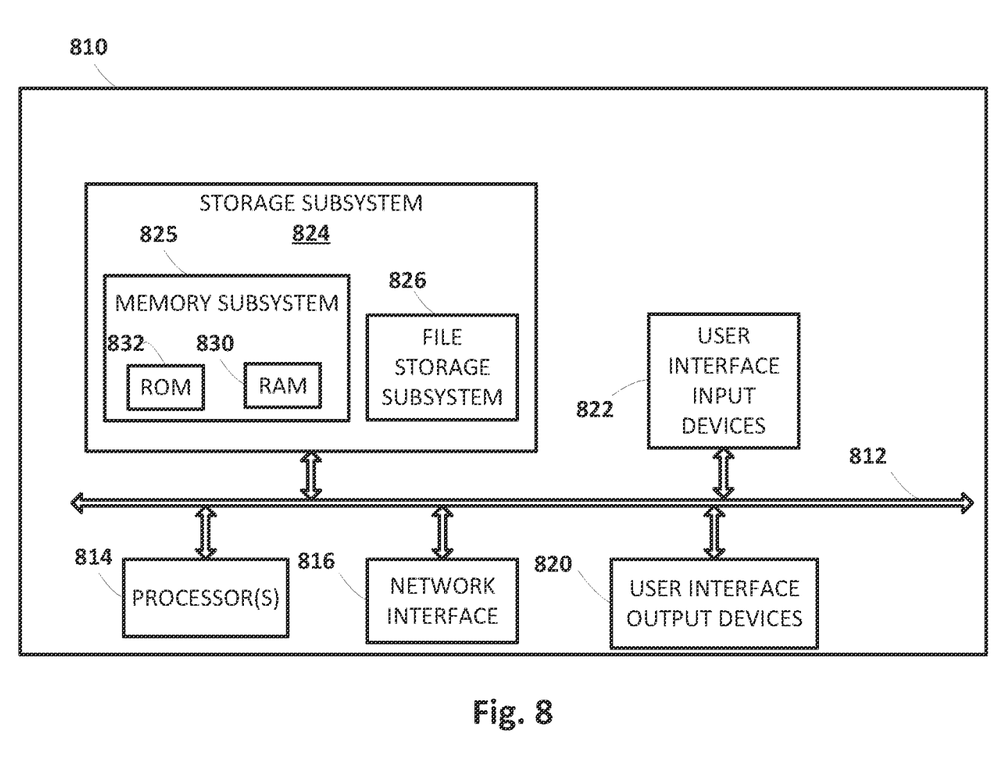
FIG. 8 depicts an example computer system architecture on which selected aspects of the present disclosure may be implemented.

FIG. 8 is a block diagram of an example computing device 810 that may optionally be utilized to perform one or more aspects of techniques described herein. Computing device 810 typically includes at least one processor 814 which communicates with a number of peripheral devices via bus subsystem 812. These peripheral devices may include a storage subsystem 824, including, for example, a memory subsystem 825 and a file storage subsystem 826, user interface output devices 820, user interface input devices 822, and a network interface subsystem 816. The input and output devices allow user interaction with computing device 810. Network interface subsystem 816 provides an interface to outside networks and is coupled to corresponding interface devices in other computing devices.

User interface input devices 822 may include a keyboard, pointing devices such as a mouse, trackball, touchpad, or graphics tablet, a scanner, a touchscreen incorporated into the display, audio input devices such as voice recognition systems, microphones, and/or other types of input devices. In general, use of the term "input device" is intended to include all possible types of devices and ways to input information into computing device 810 or onto a communication network.

User interface output devices 820 may include a display subsystem, a printer, a fax machine, or non-visual displays such as audio output devices. The display subsystem may include a cathode ray tube (CRT), a flat-panel device such as a liquid crystal display (LCD), a projection device, or some other mechanism for creating a visible image. The display subsystem may also provide non-visual display such as via audio output devices. In general, use of the term "output device" is intended to include all possible types of devices and ways to output information from computing device 810 to the user or to another machine or computing device.

Storage subsystem 824 stores programming and data constructs that provide the functionality of some or all of the modules described herein. For example, the storage subsystem 824 may include the logic to perform selected aspects of the methods of FIGS. 6-7, as well as to implement various components depicted in FIGS. 1-5.

These software modules are generally executed by processor 814 alone or in combination with other processors. Memory 825 used in the storage subsystem 824 can include a number of memories including a main random access memory (RAM) 830 for storage of instructions and data during program execution and a read only memory (ROM) 832 in which fixed instructions are stored. A file storage subsystem 826 can provide persistent storage for program and data files, and may include a hard disk drive, a floppy disk drive along with associated removable media, a CD-ROM drive, an optical drive, or removable media cartridges. The modules implementing the functionality of certain implementations may be stored by file storage subsystem 826 in the storage subsystem 824, or in other machines accessible by the processor(s) 814.

Bus subsystem 812 provides a mechanism for letting the various components and subsystems of computing device 810 communicate with each other as intended. Although bus subsystem 812 is shown schematically as a single bus, alternative implementations of the bus subsystem may use multiple busses.

Computing device 810 can be of varying types including a workstation, server, computing cluster, blade server, server farm, or any other data processing system or computing device. Due to the ever-changing nature of computers and networks, the description of computing device 810 depicted in FIG. 8 is intended only as a specific example for purposes of illustrating some implementations. Many other configurations of computing device 810 are possible having more or fewer components than the computing device depicted in FIG. 8.

Techniques described herein are not necessarily limited to estimating pain scores of human subjects. Digital twins can be created for living things other than humans, and techniques described herein may be equally applicable in, for instance, animal research and/or veterinary domains. Moreover, with regard to living things, techniques described herein may be used to train machine learning models other than pain estimation models. For example, machine learning models trained using techniques similar to those described herein may be used to predict onset of a disease flare-up, to predict the likelihood that a treatment will be successful, to predict advancement of a disease or other malady, to estimate quality of life-related factors that are difficult to quantify (e.g., pleasure of social interactions, quality of sleep, restfulness, piece of mind), etc.

Additionally, techniques described herein are not limited to estimating pain scores at all. Systems other than living things, such as robots, vehicles, aircraft, spaceships, water vehicles, etc., can be emulated using digital twins. These non-living digital twins may generate output that can be used to train a machine learning (using techniques described herein) to estimate other metrics pertinent to non-living systems, such as risk-of-failure, time-to-failure, cost-to-operate, likelihood of success, etc.

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying." "having." "containing," "involving." "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03. It should be understood that certain expressions and reference signs used in the claims pursuant to Rule 6.2(b) of the Patent Cooperation Treaty ("PCT") do not limit the scope.

What is claimed is:

1. A method implemented using one or more processors, comprising:
    applying one or more simulation parameters to a digital twin created for a subject, wherein the digital twin simulates an anatomical structure of the subject, and wherein the one or more simulation parameters cause the digital twin to generate digital twin output that simulates behavior of the anatomical structure in response to the one or more simulation parameters;
    comparing the generated digital twin output to one or more additional outputs of one or more healthy digital twins to determine at least one digital twin delta, wherein each of the one or more healthy digital twins simulates an anatomical structure in a different healthy subject;
    applying data indicative of the digital twin output as input across a pain estimation machine learning model to generate pain estimation output, wherein the pain estimation machine learning model is trained to estimate a quantification of pain that the subject would experience based on application of the simulation parameters, and wherein the pain estimation output indicates the quantification of pain, and wherein the data indicative of the digital twin output comprises the at least one digital twin delta; and
    based on the pain estimation output, rendering the quantification of pain using an output device or selecting a treatment plan.

2. The method of claim 1, wherein the pain estimation machine learning model comprises a convolutional neural network.

3. The method of claim 1, wherein the anatomical structure comprises a heart of the subject, and the digital twin output comprises an electrocardiogram ("ECG") signal.

4. The method of claim 1, wherein the one or more simulation parameters comprise a physical or daily activity.

5. The method of claim 1, wherein the one or more simulation parameters comprise a medication or therapy.

6. The method of claim 1, wherein the one or more additional outputs of one or more healthy twins comprise a plurality of additional outputs of a plurality of healthy digital twins, the at least one digital twin delta comprises a plurality of digital twin deltas, and the data indicative of the digital twin output comprises a value calculated based on the plurality of digital twin deltas.

7. The method of claim 6, wherein additional output of a first healthy digital twin of the plurality of healthy digital twins is weighted more heavily than a second additional output of a second healthy digital twin of the plurality of healthy digital twins based on one or more criteria.

8. The method of claim 7, wherein the one or more criteria include a healthy subject underlying the first healthy digital twin having a greater measure of similarity to the subject than another healthy subject underlying the second healthy digital twin.

9. At least one non-transitory computer-readable medium comprising instructions that, in response to execution of the instructions by one or more processors, cause the one or more processors to perform the method of claim 1.

* * * * *